United States Patent
Woltering

(10) Patent No.: US 8,987,255 B2
(45) Date of Patent: Mar. 24, 2015

(54) HALOGEN-ALKYL-1,3 OXAZINES AS BACE1 AND/OR BACE2 INHIBITORS

(75) Inventor: Thomas Woltering, Frelburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/116,043

(22) PCT Filed: Jun. 4, 2012

(86) PCT No.: PCT/EP2012/060457
§ 371 (c)(1),
(2), (4) Date: Nov. 6, 2013

(87) PCT Pub. No.: WO2012/168164
PCT Pub. Date: Dec. 13, 2012

(65) Prior Publication Data
US 2014/0080819 A1 Mar. 20, 2014

(30) Foreign Application Priority Data
Jun. 7, 2011 (EP) .................................. 11169007

(51) Int. Cl.
C07D 413/12 (2006.01)
A61K 31/5355 (2006.01)
A61K 31/535 (2006.01)

(52) U.S. Cl.
CPC ................................. C07D 413/12 (2013.01)
USPC ............................. 514/228.8; 544/88; 544/96

(58) Field of Classification Search
USPC .................................... 544/88, 96; 514/228.8
See application file for complete search history.

(56) References Cited

U.S. PATENT DOCUMENTS

| 2011/0046122 A1 | 2/2011 | Andreini et al. |
| 2012/0245157 A1 | 9/2012 | Masui et al. |

FOREIGN PATENT DOCUMENTS

| EP | 1942105 | 7/2008 |
| EP | 2147914 | 1/2010 |
| WO | 2006034093 | 3/2006 |
| WO | 2011069934 | 6/2011 |
| WO | 2011070029 | 6/2011 |
| WO | 2011/154431 | 12/2011 |
| WO | WO 201216816 A1 * | 12/2012 |

OTHER PUBLICATIONS

The International Search Report and Written Opinion by the International Searching Authority, issued on Jul. 16, 2012, in the PCT application No. PCT/EP2012/060457, which corresponds to the captioned application.
The letter of opposition in the corresponding Costa Rican Application No. 2013-0588, which was notified by the Costa Rican Patent Office on May 23, 2014.
The Written Opinion by the Intellectual Property Office of Singapore, issued on Nov. 3, 2014, in the corresponding Singapore Application No. 2013085659.

* cited by examiner

*Primary Examiner* — Kahsay Habte

(57) ABSTRACT

The present invention provides compounds of formula (I) having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

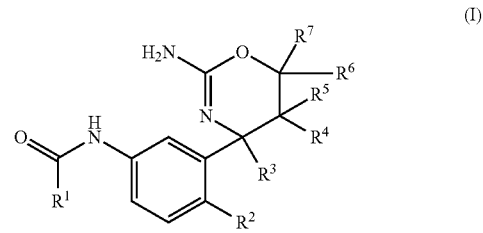

(I)

19 Claims, No Drawings

HALOGEN-ALKYL-1,3 OXAZINES AS BACE1 AND/OR BACE2 INHIBITORS

This application is a National Stage Application of PCT/EP2012/060457 filed Jun. 4, 2012, which claims priority from European Patent Application 11169007.9 filed on Jun. 7, 2011. The priority of both said PCT and European Patent Application are claimed.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem*. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes.

Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases: IBM (inclusion body myositis) (Vattemi G. et al., Lancet. 2001 Dec. 8; 358(9297): 1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci USA 2008 Jan. 29; 105(4):1291-6), Dermatomyositis (Greenberg S. A. et al., Ann Neurol. 2005 Can; 57(5):664-78 and Greenberg S. A. et al., Neurol 2005 Can; 57(5):664-78), Kaposi Sarcoma (Lagos D. et al, Blood, 2007 Feb. 15; 109 (4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 Can; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J. Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

The present invention provides novel compounds of formula I, their manufacture, medicaments based on a compound in accordance with the invention and their production as well as the use of compounds of formula I in the control or prevention of illnesses such as Alzheimer's disease and type 2 diabetes. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

FIELD OF THE INVENTION

The present invention provides halogen-alkyl-[1,3]oxazin-2-ylamines having BACE1 and/or BACE2 inhibitory properties, their manufacture, pharmaceutical compositions containing them and their use as therapeutically active substances.

SUMMARY OF THE INVENTION

The present invention provides a compounds of formula I,

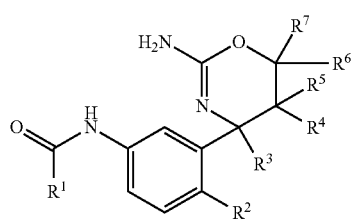

wherein the substituents and variables are as described below and in the claims, or a pharmaceutically acceptable salt thereof.

The present compounds have Asp2 (β-secretase, BACE1 or Memapsin-2) inhibitory activity and can therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. The term "$C_{1-3}$-alkyl", alone or in combination with other groups, stands for a hydrocarbon radical which can be linear or branched, wherein the alkyl group comprises 1 to 3 carbon atoms. Particular "$C_{1-6}$-alkyl" groups are "$C_{1-3}$-alkyl". Specific groups are methyl and ethyl. Most specific is methyl.

The term "halogen-$C_{1-6}$-alkyl", alone or in combination with other groups, refers to $C_{1-6}$-alkyl as defined herein, which is substituted by one or multiple halogen, in particular 1-5 halogen, more particular 1-3 halogen, most particular 1 halogen or 3 halogen. Particular halogen is fluoro. Particular "halogen-$C_{1-6}$-alkyl" is fluoro-$C_{1-6}$-alkyl. Examples are fluoromethyl, difluoromethyl, trifluoromethyl and the like. Specific groups are difluoromethyl (—CHF$_2$) or fluoromethyl (—CH$_2$F).

The term "cyano-$C_{1-6}$-alkyl", alone or in combination with other groups, refers to $C_{1-6}$-alkyl as defined herein, which is substituted by one or multiple cyano, in particular 1 cyano. Particular "cyano-$C_{1-6}$-alkyl" group is cyanomethyl.

The term "cycloalkyl-$C_{1-6}$-alkyl", alone or in combination with other groups, refers to $C_{1-6}$-alkyl as defined herein, which is substituted by one or multiple cycloalkyl as defined herein, in particular one cycloalkyl. Particular "cycloalkyl-$C_{1-6}$-alkyl" group is cyclopentyl-methyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy as defined herein, in particular 1 $C_{1-6}$-alkoxy. Particular "$C_{1-6}$-alkoxy-$C_{1-6}$-alkyl" group is methoxy-methyl.

The term "cyano", alone or in combination with other groups, refers to N≡C— (NC—).

The term "halogen", alone or in combination with other groups, denotes chloro (Cl), iodo (I), fluoro (F) and bromo (Br). Particular "halogen" groups are Cl and F. Specific group is F.

The term "heteroaryl", alone or in combination with other groups, refers to an aromatic carbocyclic group of having a single 4 to 8 membered ring or multiple condensed rings comprising 6 to 14, in particular 6 to 10 ring atoms and containing 1, 2 or 3 heteroatoms individually selected from N, O and S, in particular 1 N, in which group at least one heterocyclic ring is aromatic. Examples of "heteroaryl" groups include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" group is pyridinyl.

The term "$C_{1-6}$-alkoxy", alone or in combination with other groups, stands for an —O—$C_{1-6}$-alkyl radical which can be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (isobutoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific group is methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" groups are fluoro-$C_{1-6}$-alkoxy. Specific groups are difluoromethoxy and trifluoromethoxy.

The term "cycloalkyl-$C_{1-6}$-alkoxy", alone or in combination with other groups, refers to $C_{1-6}$-alkoxy as defined herein, which is substituted by one or multiple cycloalkyl as defined herein, in particular one cycloalkyl.

The term "$C_{2-6}$-alkenyl-$C_{1-6}$-alkoxy", alone or in combination with other groups, refers to $C_{1-6}$-alkoxy as defined herein, which is substituted by one or multiple $C_{2-6}$-alkenyl as defined herein, in particular one $C_{2-6}$-alkenyl.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular one $C_{2-6}$-alkynyl.

The term "cycloalkyl", alone or in combination with other groups, denotes a monovalent saturated monocyclic or bicyclic hydrocarbon group of 3 to 6 ring carbon atoms, particularly a monovalent saturated monocyclic hydrocarbon group of 3 to 5 ring carbon atoms. Bicyclic means consisting of two saturated carbocycles having two carbon atoms in common, i.e. the bridge separating the two rings is either a single bond or a chain of one or two carbon atoms. Particular $C_{3-6}$-cycloalkyl groups are monocyclic. Examples are cyclopropyl, cyclobutanyl, cyclopentyl, cyclohexyl or cycloheptyl.

Examples for bicyclic cycloalkyl are bicyclo[2.2.1]heptanyl, bicyclo[2.2.2]octanyl or adamantanyl. Particular "cycloalkyl" groups are cyclopropyl or cyclopentyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one or two triple bonds. Examples of $C_{2-6}$-alkynyl include ethynyl, propynyl, prop-2-ynyl and n-butynyl. Specific group is prop-2-ynyl.

The term "halogen-$C_{2-6}$-alkynyl", alone or in combination with other groups, refers to $C_{2-6}$-alkynyl as defined herein, which is substituted by one or multiple halogen, in particular 1-5 halogen, more particular 1-3 halogen, most particular one halogen or 3 halogens. Particular halogen is fluoro.

The term "cyano-$C_{2-6}$-alkynyl", alone or in combination with other groups, refers to $C_{2-6}$-alkynyl as defined herein, which is substituted by one or multiple cyano, in particular one cyano.

The term "cycloalkyl-$C_{2-6}$-alkynyl", alone or in combination with other groups, refers to $C_{2-6}$-alkynyl as defined herein, which is substituted by one or multiple cycloalkyl as defined herein, in particular one cycloalkyl.

The term "$C_{1-6}$-alkoxy-$C_{2-6}$-alkynyl", alone or in combination with other groups, refers to $C_{2-6}$-alkynyl as defined herein, which is substituted by one or multiple $C_{1-6}$-alkoxy as defined herein, in particular one $C_{1-6}$-alkoxy.

The term "$C_{2-6}$-alkenyl", alone or in combination with other groups, denotes a monovalent linear or branched saturated hydrocarbon group of 2 to 6 carbon atoms, in particular from 2 to 4 carbon atoms, and comprising one, two or three double bonds. Examples of $C_{2-6}$-alkenyl include ethenyl, propenyl and the like.

The term "halogen-$C_{2-6}$-alkenyl", alone or in combination with other groups, refers to $C_{2-6}$-alkenyl as defined herein, which is substituted by one or multiple halogen, in particular 1-5 halogen, more particular 1-3 halogen, most particular one halogen or 3 halogen. Particular halogen is fluoro.

The term "cyano-$C_{2-6}$-alkenyl", alone or in combination with other groups, refers to $C_{2-6}$-alkenyl as defined herein, which is substituted by one or multiple cyano, in particular one cyano.

The term "cycloalkyl-$C_{2-6}$-alkenyl", alone or in combination with other groups, refers to $C_{2-6}$-alkenyl as defined herein, which is substituted by one or multiple cycloalkyl as defined herein, in particular one cycloalkyl.

The term "$C_{1-6}$-alkoxy-$C_{2-6}$-alkenyl", alone or in combination with other groups, refers to $C_{2-6}$-alkenyl as defined herein, which is substituted by one or multiple $C_{1-6}$-alkoxy as defined herein, in particular one $C_{1-6}$-alkoxy.

The term "aryl" denotes a monovalent aromatic carbocyclic mono- or bicyclic ring system comprising 6 to 10 carbon ring atoms. Examples of aryl moieties include phenyl and naphthyl. Specific group is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product can not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" (here also $P^1$) denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments can be combined.

One embodiment of the invention is a compound of formula I,

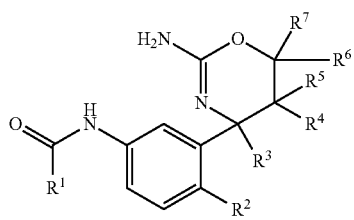

I wherein $R^1$ is aryl or heteroaryl, each unsubstituted or substituted by 1-4 substituents individually selected from $C_{1-6}$-alkyl, cyano, cyano-$C_{1-6}$-alkyl, cycloalkyl, cycloalkyl-$C_{2-6}$-alkenyl, cycloalkyl-$C_{2-6}$-alkynyl, cycloalkyl-$C_{1-6}$-alkyl, cycloalkyl-$C_{1-6}$-alkoxy, halogen, halogen-$C_{2-6}$-alkenyl, halogen-$C_{2-6}$-alkynyl, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{1-6}$-alkoxy-$C_{2-6}$-alkenyl, $C_{1-6}$-alkoxy-$C_{2-6}$-alkynyl, $C_{2-6}$-alkenyl, $C_{2-6}$-alkynyl, $C_{2-6}$-alkenyl-$C_{1-6}$-alkoxy and $C_{2-6}$-alkynyl-$C_{1-6}$-alkoxy;

$R^2$ is selected from the group consisting of
  i) hydrogen, and
  ii) halogen, $R^3$ is halogen-$C_{1-6}$-alkyl;

$R^4$ and $R^5$ are both hydrogen or both halogen;

$R^6$ is selected from the group consisting of
  i) hydrogen, and
  ii) $C_{1-6}$-alkyl, $R^7$ is selected from the group consisting of
  i) hydrogen, and
  ii) $C_{1-6}$-alkyl, or pharmaceutically acceptable salts thereof.

A certain embodiment of the invention provides a compound of formula I as described herein, wherein $R^1$ is heteroaryl substituted by 1-2 substituents individually selected from $C_{1-6}$-alkyl, cyano, cyano-$C_{1-6}$-alkyl, cycloalkyl, cycloalkyl-$C_{2-6}$-alkenyl, cycloalkyl-$C_{2-6}$-alkynyl, cycloalkyl-$C_{1-6}$-alkyl, cycloalkyl-$C_{1-6}$-alkoxy, halogen, halogen-$C_{2-6}$-alkenyl, halogen-$C_{2-6}$-alkynyl, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{1-6}$-alkoxy-$C_{2-6}$-alkenyl, $C_{1-6}$-alkoxy-$C_{2-6}$-alkynyl, $C_{2-6}$-alkenyl, $C_{2-6}$-alkynyl, $C_{2-6}$-alkenyl-$C_{1-6}$-alkoxy and $C_{2-6}$-alkynyl-$C_{1-6}$-alkoxy.

A certain embodiment of the invention provides a compound of formula I as described herein, wherein $R^1$ is pyridinyl substituted by cyano.

A certain embodiment of the invention provides a compound of formula I as described herein, wherein $R^1$ is 5-cyano-pyridine-2-yl.

A certain embodiment of the invention provides a compound of formula I as described herein, wherein $R^2$ is hydrogen.

A certain embodiment of the invention provides a compound of formula I as described herein, wherein $R^2$ is halogen.

A certain embodiment of the invention provides a compound of formula I as described herein, wherein $R^2$ is F.

A certain embodiment of the invention provides a compound of formula I as described herein, wherein $R^3$ is fluoro-$C_{1-6}$-alkyl.

A certain embodiment of the invention provides a compound of formula I as described herein, wherein $R^3$ is —CHF$_2$.

A certain embodiment of the invention provides a compound of formula I as described herein, wherein $R^3$ is —CH$_2$F.

A certain embodiment of the invention provides a compound of formula I as described herein, wherein $R^4$ and $R^5$ are halogen.

A certain embodiment of the invention provides a compound of formula I as described herein, wherein $R^4$ and $R^5$ are F.

A certain embodiment of the invention provides a compound of formula I as described herein, wherein $R^4$ and $R^5$ are H.

A certain embodiment of the invention provides a compound of formula I as described herein, wherein $R^6$ is H.

A certain embodiment of the invention provides a compound of formula I as described herein, wherein $R^6$ is $C_{1-6}$-alkyl.

A certain embodiment of the invention provides a compound of formula I as described herein, wherein $R^6$ is methyl.

A certain embodiment of the invention provides a compound of formula I as described herein, wherein $R^7$ is H.

A certain embodiment of the invention provides a compound of formula I as described herein, wherein $R^7$ is $C_{1-6}$-alkyl.

A certain embodiment of the invention provides a compound of formula I as described herein, wherein $R^7$ is methyl.

A certain embodiment of the invention provides a compound of formula I as described herein, which is (S)—N-(3-(2-amino-4-(difluoromethyl)-5,6-dihydro-4H-1,3-oxazin-4-yl)-4-fluorophenyl)-5-cyanopicolinamide.

A certain embodiment of the invention provides a process for preparing a compound of formula I as defined herein, which process comprises reacting a compound of formula I' to a compound of formula I

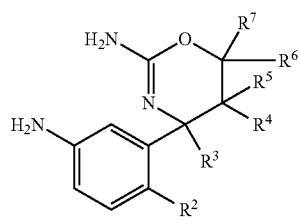

wherein $R^2$, $R^3$, $R^4$, $R^5$, $R^6$ and $R^7$ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of diabetes, which method comprises administering a compound of formula I as described herein to a human being or animal.

A certain embodiment of the invention provides a method for the use in the therapeutic and/or prophylactic treatment of type 2 diabetes, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

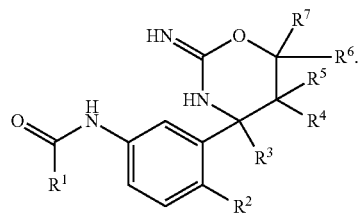

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Stereoisomers of compounds of formula I are compounds of formula Ia or compounds of formula Ib, in particular compounds of formula Ia, wherein the residues have the meaning as described in any of the embodiments.

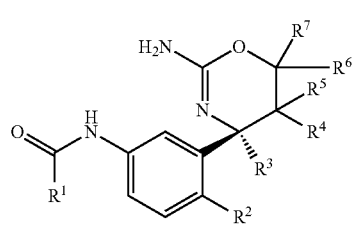

Ia

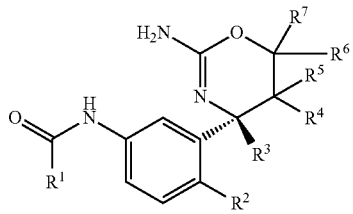

Ib

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Difluoroketones of general formula E1 can be prepared by reaction of an aryllithium or arylmagnesium compound with ethyl difluoroacetate as described in Tetrahedron 2005, 61(19), 4671 and J. Org. Chem. 2006, 71(9), 3545.

Sulfinyl imines of general formula E2 can be prepared in analogy to T. P. Tang & J. A. Ellman, J. Org. Chem. 1999, 64, 12, by condensation of an aryl ketone E1 and a sulfinamide, e.g. an alkyl sulfinamide, most particularly (S)-(−)- or (R)-(+)-tert-butylsulfinamide, in the presence of a Lewis acid such as e.g. a titanium(IV)alkoxide, more particularly titanium(IV)ethoxide in a solvent such as an ether, e.g. diethyl ether or more particularly tetrahydrofuran.

The conversion of the sulfinyl imine E2 to the sulfinamide ester E3 can proceed stereoselectively by the chiral directing group as described by Tang & Ellman. The sulfinyl imine E2 can be reacted in a Reformatsky reaction with a zinc enolate, activated zinc powder at ambient to elevated temperature, particularly at 23 to 60° C. in a solvent such as an ether, e.g. diethyl ether or more particularly tetrahydrofuran. The zinc enolate is generated from an alkyl bromoacetate or propionate optionally substituted by additional halogen, e.g. particularly ethyl bromoacetate, ethyl bromo-fluoro-acetate, ethyl bromodifluoroacetate or ethyl 2-bromo-2-fluoro-propionate. The sulfinyl imine E2 can also be reacted with an alkyl acetate optionally substituted by a halogen-alkoxy group, like e.g. methyl acetate or ethyl 2-(2,2,2-trifluoroethoxy)acetate, in presence of a strong base such as lithium diisopropylamide at 0 to −78° C. in the presence of a titanium(IV) reagent such as chlorotitaniumtriisopropoxide an inert solvent such as an ether, e.g. diethyl ether or more particularly tetrahydrofuran.

The alcohol of formula E4 can be prepared by the reduction of an ethylester of formula E3 with an alkali hydride, particularly lithium borohydride or lithium aluminum hydride, in a solvent such as an ether, e.g. diethyl ether or more particularly tetrahydrofuran.

Hydrolysis of the chiral directing group in the sulfinamide alcohol of formula E4 to give the aminoalcohol of formula E5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula E6 can be prepared by reaction of an aminoalcohol of formula E5 with cyanogen bromide in a solvent such as an alcohol, particularly ethanol.

Protection of the amino group in compounds of formula E6 to produce aryl bromides of formula E7 can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), particularly DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of formula E7 can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-PHOS), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of formula E8.

Deprotection of both amino groups in compounds of formula E8 can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the P$^1$-group. Then the addition of water to cleave the benzophenone imine and reaction at ambient temperature produces diamines of formula E9.

Amide coupling of diamines of formula E9 and carboxylic acids to give amides of formula I.2 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimethylformamide, at temperatures between 0° C. and ambient temperature.

Scheme E: Synthesis of compounds of formula I.2.

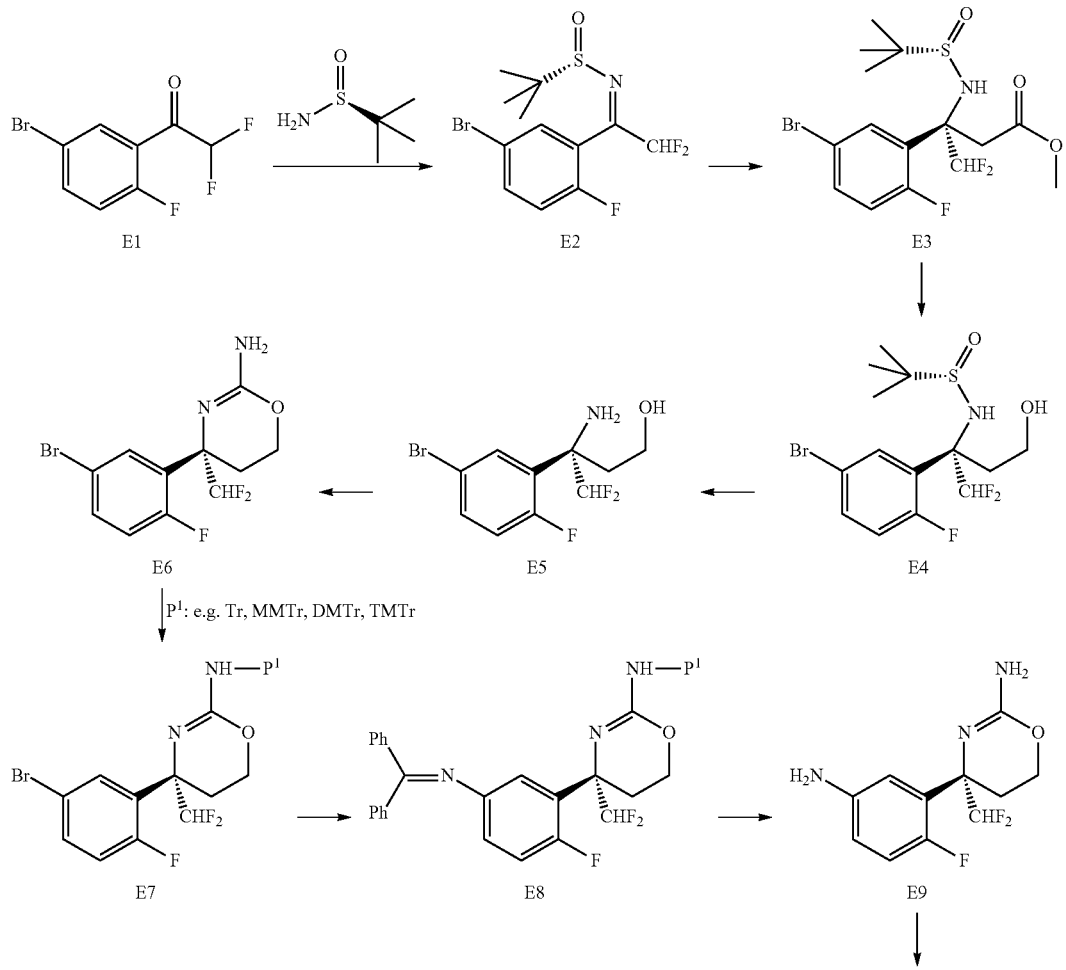

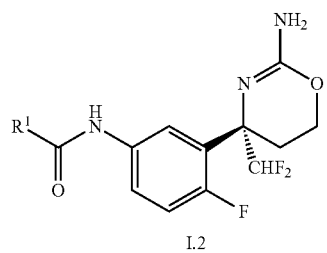

I.2

Fluoroketones of general formula F1 can be prepared by reaction of the corresponding hydroxyketones with e.g. nonafluoro-n-butanesulfonyl fluoride and triethylamine trihydrofluoride in presence of an organic base, e.g. triethylamine, in inert solvents like toluene or chlorinated solvents, e.g. dichloroethane or dichloromethane, preferably dichloromethane, at temperatures between −20 and 30° C., preferably at 0° C.

Sulfinyl imines of general formula F2 can be prepared in analogy to T. P. Tang & J. A. Ellman, J. Org. Chem. 1999, 64, 12, by condensation of an aryl ketone F1 and a sulfinamide, e.g. an alkyl sulfinamide, most particularly (S)-(−)- or (R)-(+)-tert-butylsulfinamide, in the presence of a Lewis acid such as e.g. a titanium(IV)alkoxide, more particularly titanium(IV)ethoxide in a solvent such as an ether, e.g. diethyl ether or more particularly tetrahydrofuran.

The conversion of the sulfinyl imine F2 to the sulfinamide ester F3 can proceed stereoselectively by the chiral directing group as described by Tang & Ellman. The sulfinyl imine F2 can be reacted in a Reformatsky reaction with a zinc enolate, activated zinc powder at ambient to elevated temperature, particularly at 23 to 60° C. in a solvent such as an ether, e.g. diethyl ether or more particularly tetrahydrofuran. The zinc enolate is generated from an alkyl bromoacetate or propionate optionally substituted by additional halogen, e.g. particularly ethyl bromoacetate, ethyl bromo-fluoro-acetate, ethyl bromodifluoroacetate or ethyl 2-bromo-2-fluoro-propionate.

The alcohol of formula F4 can be prepared by the reduction of an ethylester of formula F3 with an alkali hydride, particularly lithium borohydride or lithium aluminum hydride, in a solvent such as an ether, e.g. diethyl ether or more particularly tetrahydrofuran.

Hydrolysis of the chiral directing group in the sulfinamide alcohol of formula F4 to give the aminoalcohol of formula F5 can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula F6 can be prepared by reaction of an aminoalcohol of formula F5 with cyanogen bromide in a solvent such as an alcohol, particularly ethanol.

The nitro derivative of formula F7 can be prepared by nitration of the oxazine F6 following a standard procedure involving neat sulfuric acid and fuming nitric acid without using a solvent.

The reduction of the nitro group in compounds of formula F7 to give anilines of formula F8 can be accomplished by hydrogenation using a catalyst, such as palladium on carbon, in protic solvents, such as alcohols, in particular ethanol or methanol.

Amide coupling of diamines of formula F8 and carboxylic acids to give amides of formula I.3 can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium.-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimethylformamide, at temperatures between 0° C. and ambient temperature.

Scheme F: Synthesis of compounds of formula I.3.

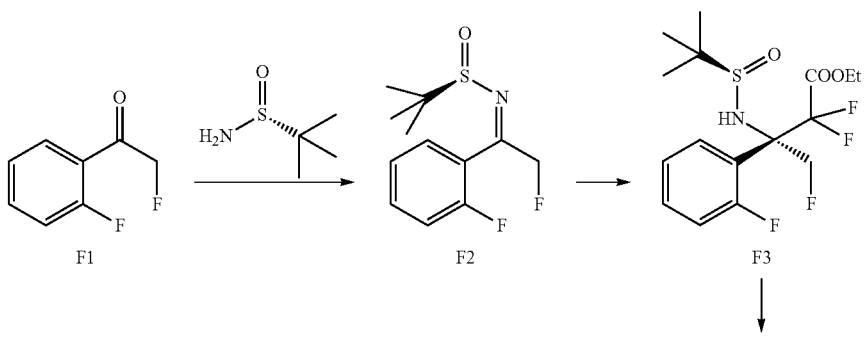

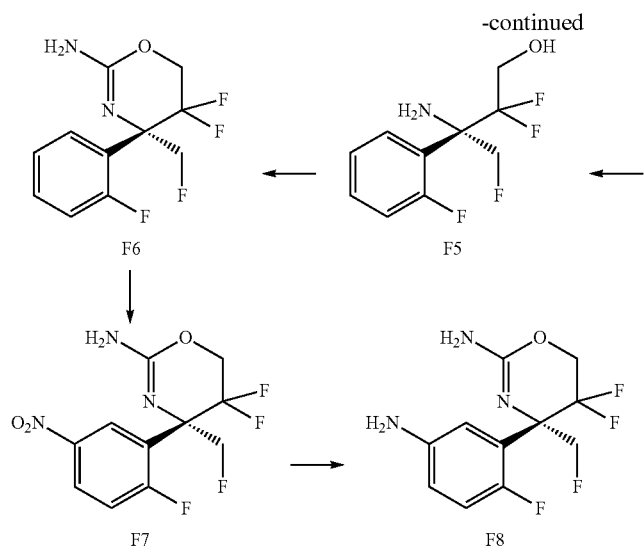
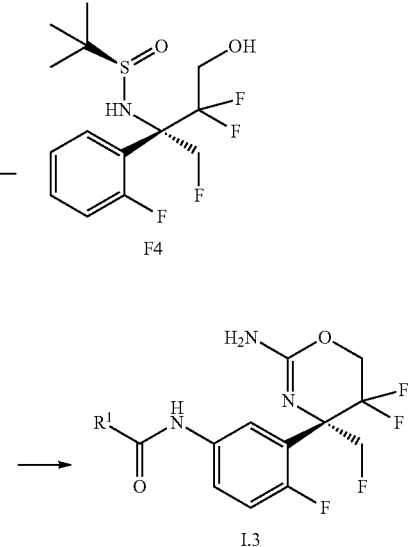

The corresponding pharmaceutically acceptable salts with acids can be obtained by standard methods known to the person skilled in the art, e.g. by dissolving the compound of formula I in a suitable solvent such as e.g. dioxane or tetrahydrofuran (THF) and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ0 peptide.

b) Alternatively, the Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat#AL275C).

In a Perkin-Elmer White Optiplate-384 (Cat#6007290), 2 ul culture supernatants were combined with 2 μl of a 10× AlphaLISA Anti-hAβAcceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

For example, an $IC_{50}$ value of 0.0039 µM was obtained for example 1 (BACE1 cell act. Aβ40) and for example 2 an $IC_{50}$ value of 0.40 µM was obtained.

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

EXAMPLE A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |

TABLE 2-continued possible capsule ingredient composition

| ingredient | mg/capsule | | | |
| --- | --- | --- | --- | --- |
| | 5 | 25 | 100 | 500 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
| --- | --- |
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 6 possible injection solution composition

| ingredient | mg/injection solution. |
| --- | --- |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Synthesis of the Intermediate Difluoroketones E1

Intermediate E1.1

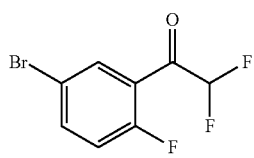

A solution of diisopropylamine (12.7 g, 17.9 ml, 126 mmol) and tetrahydrofuran (375 ml) was cooled to −78° C. and n-BuLi (1.6 M in hexane) (78.6 ml, 126 mmol) was added dropwise. After stirring for 10 min commercially available 1-bromo-4-fluorobenzene {CAS[460-00-4]} (20 g, 12.4 ml, 114 mmol) was added dropwise at max. −60° C. Stirring was continued at −70° C. for 2.5 hours. Then ethyl difluoroacetate (17.0 g, 13.7 ml, 137 mmol) was added dropwise and the mixture was warmed to −10° C. and then quenched by pouring the mixture onto 1 M HCl. The mixture was extracted twice with ethyl acetate, dried over sodium sulphate, filtered and evaporated to give a yellow liquid (34 g; 118%). The residue was chromatographed on 200 g silica gel with cyclohexane/ethyl acetate 3:1 to give 1-(5-bromo-2-fluorophenyl)-2,2-difluoroethanone (26.5 g, 105 mmol, 91.6% yield) as a yellow liquid. MS (EI): m/z=252.0 [M]$^+$ and 254.0 [M+2]$^+$.

Synthesis of the Intermediate Sulfinyl Imines E2

Intermediate E2.1

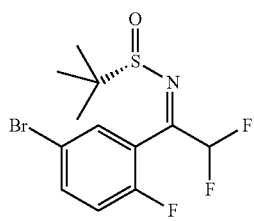

To a solution of 1-(5-bromo-2-fluorophenyl)-2,2-difluoroethanone (intermediate E1.1) (13.2 g, 52.2 mmol) and (S)-(−)-2-methyl-2-propanesulfinamide (6.96 g, 57.4 mmol) in tetrahydrofuran (104 ml) was added at 23° C. titanium(IV) ethoxide (21.4 g, 19.5 ml, 93.9 mmol). The yellow solution was stirred at 70° C. for 3 hours. The cooled reaction mixture was poured into ice water, diluted with ethyl acetate and filtered through a pad of Dicalite. The organic layer was separated and washed with brine and then dried over Na$_2$SO$_4$. Removal of the solvent in vacuum left a yellow oil (18.25 g), which was purified by silica column chromatography 200 g, SiO$_2$ with dichloromethane/heptane 1:1 to give (S,E)-N-(1-(5-bromo-2-fluorophenyl)-2,2-difluoroethylidene)-2-methylpropane-2-sulfinamide (14.49 g, 40.7 mmol, 78.0% yield) as a yellow oil. MS (ISP): m/z=355.9 [M+H]$^+$ and 357.9 [M+2+H]$^+$.

Syntheses of the Intermediate Sulfinamide Esters E3.1 and E3.2

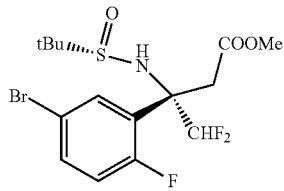

E3.1

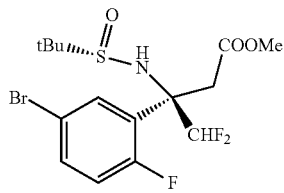

E3.2

To a solution of diisopropylamine (6.52 g, 9.19 ml, 64.5 mmol) in tetrahydrofuran (115 ml) was added at −70° C. n-BuLi (1.6 M in hexane) (40.3 ml, 64.5 mmol) dropwise and stirring was continued for 15 min at −70° C. The solution was treated with methyl acetate (4.77 g, 5.13 ml, 64.5 mmol) and after 30 min chlorotitanium triisopropoxide (0.85 M in THF) (85.7 ml, 72.85 mmol) was added dropwise and stirring was continued at −70° C. for 30 min. The mixture was treated with a solution of (S,E)-N-(1-(5-bromo-2-fluorophenyl)-2,2-difluoroethylidene)-2-methylpropane-2-sulfinamide (intermediate E2.1) (8.2 g, 23.0 mmol) in tetrahydrofuran (76.4 ml) and stirring was continued at −70° C. for 2 hours. The mixture was quenched with saturated aqueous NH$_4$Cl solution (100 ml), diluted with ethyl acetate (200 ml) and the mixture was filtered over dicalite. The organic layer was separated and washed with water and brine. The aqueous layers were rextracted with ethyl acetate. The combined organic layers were dried over Na$_2$SO$_4$, filtered and evaporated to give a yellow oil (11.5 g; 116%). The residue was chromatographed on 50 g silica gel with ethyl acetate/heptane 0-50% to give a 1:1 diastereomeric mixture of methyl 3-(5-bromo-2-fluorophenyl)-3-((S)-1,1-dimethylethylsulfinamido)-4,4-difluorobutanoate (7 g, 16.3 mmol, 70.7% yield) as a colourless oil. MS (ISP): m/z=430.2 [M+H]$^+$ and 432.1 [M+2+H]$^+$.

Chiral separation of methyl 3-(5-bromo-2-fluorophenyl)-3-((S)-1,1-dimethylethylsulfinamido)-4,4-difluorobutanoate (3.8 g, 8.83 mmol) by preparative chiral HPLC on Reprosil Chiral NR column with eluent 5% EtOH/n-heptane to give (S)-methyl 3-(5-bromo-2-fluorophenyl)-3-((S)-1,1-dimethylethylsulfinamido)-4,4-difluorobutanoate (1.55 g, 3.6 mmol, 40.8% yield) as a colourless oil and (R)-methyl 3-(5-bromo-2-fluorophenyl)-3-(S)-1,1-dimethylethylsulfinamido)-4,4-difluorobutanoate (1.65 g, 3.83 mmol, 43.4% yield) as a colorless oil.

Synthesis of the Intermediate Sulfinamide Alcohols E4

Intermediate E4.1

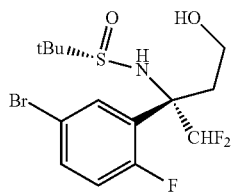 [SMILES: CC(C)(C)[S@](=O)N[C@@](CCO)(c1cc(Br)ccc1F)C(F)F]

(S)-methyl 3-(5-bromo-2-fluorophenyl)-3-((S)-1,1-dimethylethylsulfinamido)-4,4-difluorobutanoate (intermediate E3.1) (1.65 g, 3.83 mmol) was dissolved in tetrahydrofuran (80 ml) and lithium borohydride (668 mg, 30.7 mmol) was added at 5° C. in two portions. The turbid solution was stirred at 23° C. for 16 hours. The reaction mixture was poured into ice water and ethyl acetate was added. Saturated NH$_4$Cl solution (50 ml) was added slowly and the mixture was stirred vigorously for 45 min until the gas evolution finished. The organic layer was separated, dried over Na$_2$SO$_4$, filtered and evaporated to give a yellow oil. The residue was purified by chromatography on 50 g silica gel with ethyl acetate/heptane 0-80% to give (S)—N—((S)-2-(5-bromo-2-fluorophenyl)-1,1-difluoro-4-hydroxybutan-2-yl)-2-methylpropane-2-sulfinamide (815 mg, 2.03 mmol, 52.8% yield) as a colourless oil. MS (ISN): m/z=399.9 [M–H]$^-$ and 401.9 [M+2–H]$^-$.

Synthesis of the Intermediate Amino Alcohols E5

Intermediate Amino Alcohol E5.1

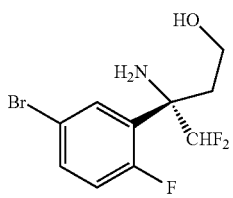 [SMILES: N[C@@](CCO)(c1cc(Br)ccc1F)C(F)F]

To a solution of (S)—N—((S)-2-(5-bromo-2-fluorophenyl)-1,1-difluoro-4-hydroxybutan-2-yl)-2-methylpropane-2-sulfinamide (intermediate E4.1) (810 mg, 2.01 mmol) in THF (40 ml) was added conc. HCl (595 mg, 496 µl, 6.04 mmol) at 23° C. The mixture was stirred for 4 hours at 23° C. Poured into 1 M Na$_2$CO$_3$-solution, extracted with ethyl acetate and dried over Na$_2$SO$_4$. Removal of solvent in vacuum left (S)-3-amino-3-(5-bromo-2-fluorophenyl)-4,4-difluorobutan-1-ol (570 mg, 1.91 mmol, 95.0% yield) as a light yellow oil. The crude product was used in the next step without further purification. MS (ISP): m/z=298.1 [M+H]$^+$ and 300.1 [M+2+H]$^+$.

Syntheses of the Intermediate Amino Oxazines E6

Intermediate Amino Oxazine E6.1

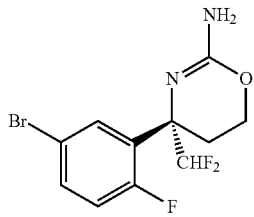 [SMILES: NC1=N[C@@](c2cc(Br)ccc2F)(C(F)F)CCO1]

To a solution of (S)-3-amino-3-(5-bromo-2-fluorophenyl)-4,4-difluorobutan-1-ol (intermediate E5.1) (570 mg, 1.91 mmol) in ethanol (10 ml) was added under Argon cyanogen bromide (313 mg, 2.87 mmol) at 23° C. The mixture was stirred in a sealed tube for 16 hours at 80° C. Poured into ice water and saturated. NaHCO$_3$-solution and then extracted with dichloromethane. The organic layer was dried over Na$_2$SO$_4$, filtered and evaporated to give a light yellow oil (620 mg), which was purified by flash chromatography on 20 g silica gel with ethyl acetate/heptane 0-50% to give (S)-4-(5-bromo-2-fluorophenyl)-4-(difluoromethyl)-5,6-dihydro-4H-1,3-oxazin-2-amine (250 mg, 774 µmol, 40.5% yield) as a white solid. MS (ISP): m/z=323.0 [M+H]$^+$ and 325.0 [M+2+H]$^+$.

Synthesis of the Intermediate DMTr-Protected Amino Oxazines E7

Intermediate E7.1

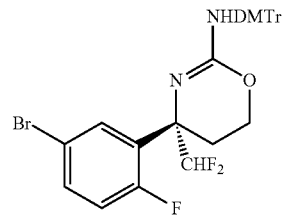

To a solution of (S)-4-(5-bromo-2-fluorophenyl)-4-(difluoromethyl)-5,6-dihydro-4H-1,3-oxazin-2-amine (intermediate E6.1) (372 mg, 1.15 mmol) in dichloromethane (10 ml) was added at 0° C. 4,4'-(chloro(phenyl)methylene)bis(methoxybenzene) (585 mg, 1.73 mmol). The reaction mixture was stirred at 23° C. for 16 hours. Extraction with water, then drying of the organic layer over Na$_2$SO$_4$, filtration, evaporation. Chromatography on 20 g silica gel with ethyl acetate/heptane 0-50% gave the (S)—N-(bis(4-methoxyphenyl)(phenyl)methyl)-4-(5-bromo-2-fluorophenyl)-4-(difluoromethyl)-5,6-dihydro-4H-1,3-oxazin-2-amine (725 mg, 1.1 mmol, 95.6% yield) as a white foam. MS (ISP): m/z=625.2 [M+H]$^+$ and 627.3 [M+2+H]$^+$.

Synthesis of the Intermediate Imines E8

Intermediate E8.1

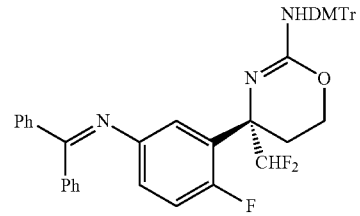

Under argon in a sealed tube were added to a solution of (S)—N-(bis(4-methoxyphenyl)(phenyl)methyl)-4-(5-bromo-2-fluorophenyl)-4-(difluoromethyl)-5,6-dihydro-4H-1,3-oxazin-2-amine (intermediate E7.1) (725 mg, 1.16 mmol) in toluene (15 ml) sodium tert-butoxide (334 mg, 3.48 mmol), 2-di-tert-butylphosphino-2',4',6'-triisopropylbiphenyl (73.8 mg, 174 µmol) and tris(dibenzylideneacetone)dipalladium(0) chloroform adduct (60.0 mg, 58.0 µmol) and benzophenone imine (420 mg, 389 µl, 2.32 mmol), the tube was sealed under argon and the mixture was stirred at 105° C. for 4 h. The brown solution was extracted with ethyl acetate/water. The organic layer was washed with brine, dried over Na$_2$SO$_4$, filtered and evaporated to give a brown oil. The residue was chromatographed on 20 g silica gel with ethyl acetate 0-50% to give (S)—N-(bis(4-methoxyphenyl)(phenyl)methyl)-4-(difluoromethyl)-4-(5-(diphenylmethyleneamino)-2-fluorophenyl)-5,6-dihydro-4H-1,3-oxazin-2-amine (525 mg, 723 µmol, 62.4% yield) as a yellow oil. MS (ISP): m/z=726.8 [M+H]$^+$.

Syntheses of the Intermediate Anilines E9
Intermediate aniline E9.1

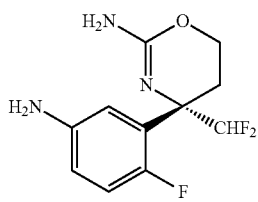 [SMILES: NC1=N[C@@](c2cc(N)ccc2F)(C(F)F)CCO1]

To a solution of (S)—N-(bis(4-methoxyphenyl)(phenyl)methyl)-4-(difluoromethyl)-4-(5-(diphenylmethyleneamino)-2-fluorophenyl)-5,6-dihydro-4H-1,3-oxazin-2-amine (intermediate E8.1) (525 mg, 723 µmol) in dichloromethane (20 ml) was added at 23° C. trifluoroacetic acid (4.12 g, 2.79 ml, 36.2 mmol) and the mixture was stirred at 23° C. for 1 hour, whereupon 1 M HCl (14.5 ml, 14.5 mmol) and dioxane (40 ml) were added and the mixture was stirred vigorously at 23° C. for 60 hours. Poured into 1 M $Na_2CO_3$-solution, extracted with dichloromethane, washed the organic layer with brine and dried over $Na_2SO_4$. Removal of the solvent in vacuum left a brown oil. The residue was purified by chromatography on 5 g silica gel with dichloromethane/methanol/ammonium hydroxide 110:10:1 to give (S)-4-(5-amino-2-fluorophenyl)-4-(difluoromethyl)-5,6-dihydro-4H-1,3-oxazin-2-amine (82 mg, 316 µmol, 43.7% yield) as a light brown solid. MS (ISP): m/z=259.9 [M+H]$^+$.

Synthesis of the Intermediate Fluoroketones F1
Intermediate F1.1

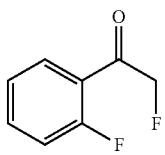 [SMILES: O=C(CF)c1ccccc1F]

A solution of 1-(2-fluorophenyl)-2-hydroxyethanone [CAS 218771-68-7; WO9857925, ex. 16] (2.77 g, 18.0 mmol) in dichloromethane (42 ml) was treated consecutively at 0° C. with triethylamine (6.36 g, 62.8 mmol), triethylamine trihydrofluoride (3.05 g, 18.0 mmol) and nonafluoro-n-butanesulfonyl fluoride (8.48 g, 26.9 mmol). The tube was sealed and the reaction mixture stirred overnight at room temperature. For the workup, the dark red solution was poured on a saturated solution of sodium hydrogencarbonate and ice, then extracted with dichloromethane. The organic layer was separated, dried over sodium sulphate and evaporated. The crude material was purified by flash chromatography on silica gel (Telos Flash Silica) using dichloromethane as the eluent to give the 2-fluoro-1-(2-fluoro-phenyl)-ethanone (1.23 g, 61% yield) as a yellow semisolid.

Synthesis of the Intermediate Sulfinyl Imines F2
Intermediate F2.1

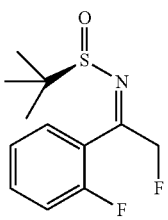 [SMILES: CC(C)(C)[S@@](=O)/N=C(/CF)c1ccccc1F]

In a manner analogous to that described for the preparation of sulfinyl imine E2.1 the reaction of 2-fluoro-1-(2-fluorophenyl)-ethanone with (R)-tert-butylsulfinamide yielded the (R)-2-methyl-propane-2-sulfinic acid [2-fluoro-1-(2-fluorophenyl)-eth-(E)-ylidene]-amide (62% yield) as an orange oil. MS (ISP): m/z=260.2 [M+H]$^+$.

Syntheses of the Intermediate Sulfinamide Esters F3
Intermediate F3.1

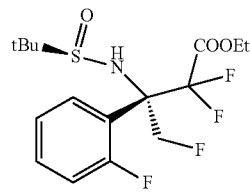 [SMILES: CCOC(=O)C(F)(F)[C@](CF)(N[S@](=O)C(C)(C)C)c1ccccc1F]

In a dry apparatus under an inert atmosphere a suspension of freshly activated zinc powder (504 mg, 7.7 mmol) and copper(I) chloride (76.4 mg, 0.77 mmol) in dry tetrahydrofuran (3 ml) was heated to reflux for 30 minutes. The suspension was cooled to room temperature and a solution of ethyl 2-bromo-2,2-difluoroacetate (391 mg, 247 µl, 1.93 mmol) in tetrahydrofuran (1.5 ml) was added dropwise. After 10 minutes a solution of (R)—N-(2-fluoro-1-(2-fluorophenyl)ethylidene)-2-methylpropane-2-sulfinamide (200 mg, 771 µmol) (intermediate F2.1) in tetrahydrofuran (1.5 ml) was added dropwise. After 1 hour the reaction mixture was cooled with ice and ethanol (80 µl) was added. The mixture was filtered over a layer of Dicalite® and the filtrate evaporated at reduced pressure. The residue was dissolved in ethyl acetate and treated consecutively with a saturated solution of ammonium chloride, sodium hydrogencarbonate and with brine. The organic layer was dried over sodium sulphate and evaporated at reduced pressure. The crude product was purified by flash chromatography on silica gel using a 2:1-mixture of heptane and ethyl acetate as the eluent to give the (S)-2,2,4-trifluoro-3-(2-fluoro-phenyl)-3-(R)-2-methyl-propane-2-sulfinylamino)-butyric acid ethyl ester (184 mg, 62% yield) as a colorless oil. MS (ISP): m/z=384.3 [M+H]$^+$.

Synthesis of the Intermediate Sulfinamide Alcohols F4
Intermediate F4.1

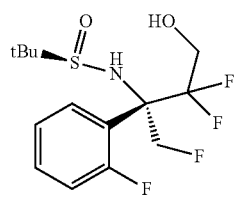 [SMILES: CC(C)(C)[S@@](=O)N[C@](CF)(c1ccccc1F)C(F)(F)CO]

(S)-2,2,4-trifluoro-3-(2-fluoro-phenyl)-3-((R)-2-methyl-propane-2-sulfinylamino)-butyric acid ethyl ester (intermediate F3.1) (177 mg, 461 µmol) was dissolved in tetrahydrofuran (4 ml) and at 0° C. lithium borohydride (2 M solution in tetrahydrofuran; (461 µl, 921 µmol) was added dropwise. After 30 minutes the reaction was complete. For the workup, the reaction mixture was poured into a mixture of ice water and a saturated solution of ammonium chloride. Thereafter, the mixture was extracted with ethyl acetate (3×), the organic layers were combined, washed with brine, dried over sodium sulphate and evaporated at reduced pressure. The resulting product was pure enough to be engaged in the next step without further purification. The 2-methyl-propane-2-sulfinic acid [(S)-2,2-difluoro-1-fluoromethyl-1-(2-fluoro-phenyl)-3-hydroxy-propyl]-amide (153 mg, 97% yield) was obtained as a white foam. MS (ISN): m/z=342.2 [M+H]$^+$.

Synthesis of the Intermediate Amino Alcohols F5

Intermediate Amino Alcohol F5.1

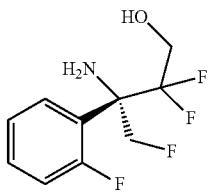 [SMILES: N[C@](CF)(c1ccccc1F)C(F)(F)CO]

A solution of 2-methyl-propane-2-sulfinic acid [(S)-2,2-difluoro-1-fluoromethyl-1-(2-fluoro-phenyl)-3-hydroxy-propyl]-amide (intermediate F4.1) (145.5 mg, 426 µmol) in methanol (2.5 ml) was cooled to 0° C. and treated with hydrochloric acid (4 M in dioxane; (533 µl, 2.13 mmol). The solution was left to warm to room temperature and stirred for 1 hour. After removal of the solvent at reduced pressure the solid residue was dissolved in water (5 ml), then extracted with ethyl acetate (2×10 ml). The organic layers were extracted with water (5 ml), thereafter the combined aqueous layers treated with a solution of sodium carbonate (2 M) to adjust the pH to 9-10. Extraction with ethyl acetate (3×35 ml), combination of the organic layers and evaporation at reduced pressure after drying over sodium sulphate yielded the crude (S)-3-amino-2,2,4-trifluoro-3-(2-fluoro-phenyl)-butan-1-ol (78 mg, 78% yield) as a colorless oil. Evaporation of the first 2 ethyl acetate layers followed by the treatment with a solution of sodium carbonate and proceeding as described above yielded another fraction (22 mg) of product. MS (ISN): m/z=238.1 [M+H]$^+$.

Syntheses of the Intermediate Amino Oxazines F6

Intermediate Amino Oxazine F6.1

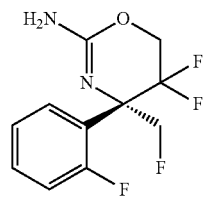 [SMILES: NC1=N[C@](CF)(c2ccccc2F)C(F)(F)CO1]

In a manner analogous to that described for the preparation of intermediate E6.1, the reaction of (S)-3-amino-2,2,4-trifluoro-3-(2-fluoro-phenyl)-butan-1-ol (intermediate F5.1) with cyanogen bromide yielded after purification by preparative HPLC the (S)-5,5-difluoro-4-fluoromethyl-4-(2-fluoro-phenyl)-5,6-dihydro-4H-[1,3]oxazin-2-ylamine (44 mg, 41% yield) as a white solid. MS (ISP): m/z=263.1 [M+H]$^+$.

Syntheses of the Intermediate Nitro Oxazines F7

Intermediate Nitro Oxazine F7.1

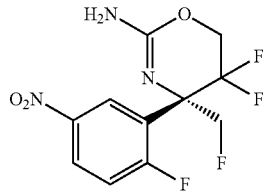 [SMILES: NC1=N[C@](CF)(c2cc([N+](=O)[O-])ccc2F)C(F)(F)CO1]

A dispersion of (S)-5,5-difluoro-4-fluoromethyl-4-(2-fluoro-phenyl)-5,6-dihydro-4H-[1,3]oxazin-2-ylamine (intermediate F6.1) (32.5 mg, 124 µmol) in sulfuric acid (1.01 g, 554 µl, 9.92 mmol) was cooled to 0° C. and stirring was continued until a complete solution was obtained. At 0° C. fuming nitric acid (12.1 mg, 8.68 µl, 174 µmol) was added in one portion and stifling continued for 2 hours. For the workup, the solution was added dropwise to a mixture of crushed ice and water. With an aqueous solution of sodium hydroxide (6 M) the pH was adjusted to 7-8. The aqueous layer was extracted three times with ethyl acetate, thereafter the combined organic layers were washed with brine, then dried over sodium sulphate and evaporated at reduced pressure. The (S)-5,5-difluoro-4-fluoromethyl-4-(2-fluoro-5-nitro-phenyl)-5,6-dihydro-4H-[1,3]oxazin-2-ylamine (39 mg, quantitative yield) was obtained as a light yellow solid and was engaged in the following step without further purification. MS (ISP): m/z=308.3 [M+H]$^+$.

Syntheses of the Intermediate Anilines F8

Intermediate Aniline F8.1

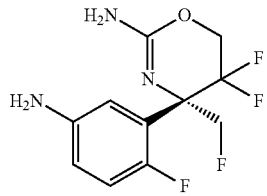

A solution of (S)-5,5-difluoro-4-fluoromethyl-4-(2-fluoro-5-nitro-phenyl)-5,6-dihydro-4H-[1,3]oxazin-2-ylamine (intermediate F7.1) (38.2 mg, 120 µmol) in ethanol (2 ml) was hydrogenated at atmospheric pressure using palladium (10% on carbon) (6.4 mg, 6 µmol) as the catalyst during 15 hours at room temperature. The reaction mixture was filtrated over a layer of Dicalite®, which was washed with ethanol (2×10 ml). The combined solutions of ethanol were evaporated at reduced pressure. The (S)-4-(5-amino-2-fluoro-phenyl)-5,5-difluoro-4-fluoromethyl-5,6-dihydro-4H-[1,3]oxazin-2-ylamine (36 mg, quantitative yield) was obtained as a light red solid and was engaged in the following step without further purification. MS (ISP): m/z=278.2 [M+H]$^+$.

EXAMPLE 1

(S)—N-(3-(2-amino-4-(difluoromethyl)-5,6-dihydro-4H-1,3-oxazin-4-yl)-4-fluorophenyl)-5-cyanopicolinamide

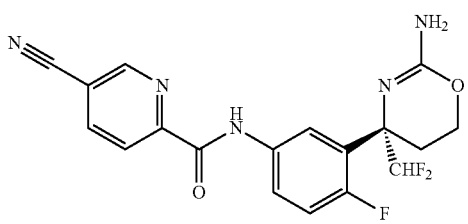 [SMILES: N#Cc1ccc(C(=O)Nc2ccc(F)c([C@]3(C(F)F)CCOC(N)=N3)c2)nc1]

To a solution of commercially available 5-cyanopicolinic acid (55.5 mg, 375 μmol) in methanol (5 ml) was added at 0° C. 4-(4,6-dimethoxy[1.3.5]triazin-2-yl)-4-methylmorpholinium chloride hydrate (129 mg, 437 μmol) and the colourless solution was stirred at 0° C. for 30 min. Then a solution of (S)-4-(5-amino-2-fluorophenyl)-4-(difluoromethyl)-5,6-dihydro-4H-1,3-oxazin-2-amine (intermediate E9.1) (81 mg, 312 μmol) in methanol (5 ml) was added dropwise at 0° C. via syringe. The reaction mixture was stirred at 23° C. for 16 h. Poured into 1 M $Na_2CO_3$-sol., extracted with dichloromethane, washed the organic layer with brine and dried over $Na_2SO_4$. Removal of the solvent in vacuum left a light brown oil which was chromatographed on 20 g silica gel with dichloromethane/methanol 0-10% to give (S)—N-(3-(2-amino-4-(difluoromethyl)-5,6-dihydro-4H-1,3-oxazin-4-yl)-4-fluorophenyl)-5-cyanopicolinamide (89 mg, 229 μmol, 73.2% yield) as a white solid. MS (ISP): m/z=390.0 $[M+H]^+$.

EXAMPLE 2

(S)—N-(3-(2-amino-5,5-difluoro-4-(fluoromethyl)-5,6-dihydro-4H-1,3-oxazin-4-yl)-4-fluorophenyl)-5-cyanopicolinamide

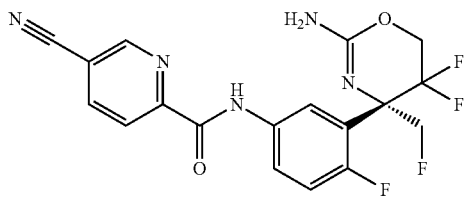 [SMILES: N#Cc1ccc(C(=O)Nc2ccc(F)c([C@@]3(CF)N=C(N)OCC3(F)F)c2)nc1]

In a manner analogous to that described in Example 1, the condensation of (S)-4-(5-amino-2-fluoro-phenyl)-5,5-difluoro-4-fluoromethyl-5,6-dihydro-4H-[1,3]oxazin-2-ylamine (intermediate F8.1) and 5-cyanopicolinic acid yielded the title compound (35 mg, 74% yield) as a light yellow foam. MS (ISP): m/z=408.4 $[M+H]^+$.

The invention claimed is:

1. A compound of formula I,

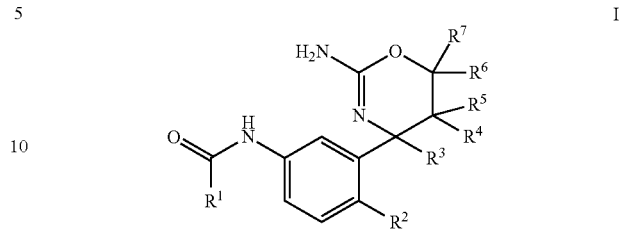

wherein $R^1$ is aryl or heteroaryl, each unsubstituted or substituted by 1-4 substituents individually selected from $C_{1-6}$-alkyl, cyano, cyano-$C_{1-6}$-alkyl, cycloalkyl, cycloalkyl-$C_{2-6}$-alkenyl, cycloalkyl-$C_{2-6}$-alkynyl, cycloalkyl-$C_{1-6}$-alkoxy, halogen, halogen-$C_{2-6}$-alkenyl, halogen-$C_{2-6}$-alkynyl, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{1-6}$-alkoxy-$C_{2-6}$-alkenyl, $C_{1-6}$-alkoxy-$C_{2-6}$-alkynyl, $C_{2-6}$-alkenyl, $C_{2-6}$-alkynyl, $C_{2-6}$-alkenyl-$C_{1-6}$-alkoxy and $C_{2-6}$-alkynyl-$C_{1-6}$-alkoxy;

$R^2$ is selected from the group consisting of
  i) hydrogen, and
  ii) halogen, $R^3$ is halogen-$C_{1-6}$-alkyl;

$R^4$ and $R^5$ are both hydrogen or both halogen;

$R^6$ is selected from the group consisting of
  i) hydrogen, and
  ii) $C_{1-6}$-alkyl, $R^7$ is selected from the group consisting of
  i) hydrogen, and
  ii) $C_{1-6}$-alkyl, or pharmaceutically acceptable salts thereof.

2. The compound according to claim 1, wherein $R^1$ is heteroaryl substituted by 1-2 substituents individually selected from $C_{1-6}$-alkyl, cyano, cyano-$C_{1-6}$-alkyl, cycloalkyl, cycloalkyl-$C_{2-6}$-alkenyl, cycloalkyl-$C_{2-6}$-alkynyl, cycloalkyl-$C_{1-6}$-alkyl, cycloalkyl-$C_{1-6}$-alkoxy, halogen, halogen-$C_{2-6}$-alkenyl, halogen-$C_{2-6}$-alkynyl, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{1-6}$-alkoxy-$C_{1-6}$-alkenyl, $C_{1-6}$-alkoxy-$C_{2-6}$-alkynyl, $C_{2-6}$-alkenyl, $C_{2-6}$-alkynyl, $C_{2-6}$-alkenyl-$C_{1-6}$-alkoxy and $C_{2-6}$-alkynyl-$C_{1-6}$-alkoxy.

3. The compound of claim 1, wherein $R^1$ is pyridinyl substituted by cyano.

4. The compound of claim 1, wherein $R^2$ is halogen.

5. The compound of claim 1, wherein $R^2$ is F.

6. The compound of claim 1, wherein $R^3$ is —$CHF_2$.

7. The compound of claim 1, wherein $R^3$ is —$CH_2F$.

8. The compound of claim 1, wherein $R^4$ and $R^5$ are H.

9. The compound of claim 1, wherein $R^4$ and $R^5$ are halogen.

10. The compound according to claim 1, wherein $R^4$ and $R^5$ are F.

11. The compound of claim 1, wherein $R^6$ is H.

12. The compound of claim 1, wherein $R^7$ is H.

13. The compound of claim 1, which is (S)—N-(3-(2-amino-4-(difluoromethyl)-5,6-dihydro-4H-1,3-oxazin-4-yl)-4-fluorophenyl)-5-cyanopicolinamide.

14. The compound of claim 1, which is (S)—N-(3-(2-amino-5,5-difluoro-4-(fluoromethyl)-5,6-dihydro-4H-1,3-oxazin-4-yl)-4-fluorophenyl)-5-cyanopicolinamide.

15. A process for preparing a compound of formula I as defined in claim 1, comprising the step of reacting a compound of formula I':

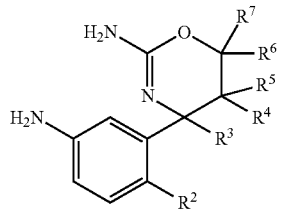

with a carboxylic acid to form the compound of formula I, wherein $R^2$, $R^3$, $R^4$, $R^5$, $R^6$ and $R^7$ are as defined in claim 1.

16. A pharmaceutical composition comprising a compound of formula I according to claim 1 and a pharmaceutically acceptable carrier and/or a pharmaceutically acceptable auxiliary substance.

17. A method of treating Alzheimer's disease, which method comprises administering a compound of formula I according to claim 1 to a human being or animal.

18. A method of treating type 2 diabetes, which method comprises administering a compound of formula I according to claim 1 to a human being or animal.

19. A method of treating amyotrophic lateral sclerosis (ALS), arterial thrombosis, breast cancer, myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I according to claim 1 to a human being or animal.

* * * * *